United States Patent [19]

Tamai et al.

[11] Patent Number: 4,656,195
[45] Date of Patent: Apr. 7, 1987

[54] ETHYLENE OXIDE ADDUCTS, METHOD OF PRODUCING SAME AND COSMETICS AND OINTMENTS CONTAINING SAME

[75] Inventors: Yoshin Tamai; Fumito Yamamoto, both of Nakajyo; Manzo Shiono; Koichi Kanehira, both of Kurashiki; Hiroshi Ozasa, Ageo; Kaoru Nomoto, Kitakawabe, all of Japan

[73] Assignee: Kuraray Co., Ltd., Kurashiki, Japan

[21] Appl. No.: 785,551

[22] Filed: Oct. 8, 1985

[30] Foreign Application Priority Data

Oct. 12, 1984 [JP] Japan ................................. 59-214979

[51] Int. Cl.$^4$ ........................ A61K 7/00; C07C 43/11
[52] U.S. Cl. .................................... 514/772; 514/785; 424/70; 424/47; 424/49; 424/63; 424/64; 424/69; 568/620; 568/623
[58] Field of Search ................ 568/620, 623; 514/772, 514/785; 424/70, 47, 49, 63, 64, 69; 252/522

[56] References Cited

U.S. PATENT DOCUMENTS 3,030,426  4/1962  Moseley et al. .................... 568/618
3,119,848  1/1964  Wrigley et al. ..................... 568/620

OTHER PUBLICATIONS

Schick, Nonionic Surfactants, Marcel Dekker, New York, 1967, p. 22.

*Primary Examiner*—Howard T. Mars
*Attorney, Agent, or Firm*—Burns, Doane, Swecker & Mathis

[57] ABSTRACT

Novel ethylene oxide adducts are provided. They have properties suited for their use as base components of cosmetics and ointments. Thus, cosmetics and ointments containing those ethylene oxide adducts are also provided. There is further provided a method of producing such ethylene oxide adducts in high yields.

4 Claims, No Drawings

ETHYLENE OXIDE ADDUCTS, METHOD OF PRODUCING SAME AND COSMETICS AND OINTMENTS CONTAINING SAME

BACKGROUND OF THE INVENTION

1. Field of the Invention

This invention relates to ethylene oxide adducts of 2,6,10,15,19,23-hexamethyltetracosane-10,15-diol. The invention also relates to a method of producing such ethylene oxide adducts. The invention further relates to cosmetics or toiletries and ointments containing such ethylene oxide adducts.

2. Description of the Prior Art

Ethylene oxide adducts of tertiary glycol containing acetylene bond represented by the general formula

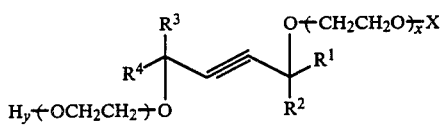

wherein $R^1$, $R^2$, $R^3$ and $R^4$ are each selected from the group consisting of alkyl, cycloalkyl, aryl and aralkyl groups provided that the total number of carbon atoms contained in those groups is at least 7 and the sum of x and y is an integer of not less than 3, are known in the art. They are produced by reacting a corresponding glycol, such as 2,4,7,9-tetramethyl-5-decyne-4,7-diol or 7,10-dimethyl-8-hexadecyne-7,10-diol, with ethylene oxide in the presence of a basic catalyst, such as triethylamine, N,N-dimethylaniline or sodium hydroxide. They are surface-active and are suited for use in those cosmetic or toiletry compositions and the like which are desired to be not very lathering, such as toothpaste, toilet soap, shampoo and detergent compositions (cf. Japanese Patent Publication No. 37-4504). However, the properties possessed by these ethylene oxide adducts are not yet satisfactory for the practical use of said adducts as base components in cosmetics.

Heretofore, there have been used hydrocarbons, such as squalane, squalene, liquid paraffin, liquid polybutene and liquid lanolin, and higher fatty acid esters, such as 2-octyldodecyl myristate, isotridecyl myristate and hexadecyl 2-ethylhexanoate, as oil-soluble base components in cosmetics. They are suited for use as such base components since they have good affinity for the human skin and adequate ability to permeate the same. As water-soluble base components in cosmetics, there are used ethylene oxide adducts derived from lanolin, castor oil and derivatives thereof. The above-mentioned oil-soluble base components in cosmetics are poor in compatibility or miscibility with water and therefore have limitations in their use. The above-mentioned water-soluble base components give sticky feeling to the skin or hair.

It is reported that the ether formation reaction between an alcohol and ethylene oxide proceeds rapidly when the alcohol is a primary one, but that such reaction proceeds very slowly when the alcohol is a secondary or tertiary one [cf. NONIONIC SURFACTANTS, pages 92–99 (1967)].

Accordingly, it is an object of the invention to provide novel ethylene oxide adducts having the excellent properties of the above-mentioned known oil-soluble base components and good water-compatibility but giving no sticky feeling. Another object of the invention is to provide a use of said novel ethylene oxide adducts as base components in cosmetics or ointments.

A further object of the invention is to provide a method of producing such novel ethylene oxide adducts in high yields by ether formation reaction between a tertiary alcohol and ethylene oxide.

These objects as well as other objects and advantages of the invention will become apparent to those skilled in the art from the following detailed description.

SUMMARY OF THE INVENTION

In accordance with one aspect of the present invention, there are provided ethylene oxide adducts of the general formula

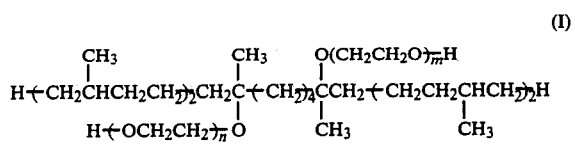

wherein the mean value of the sum of m and n falls within the range of 10 to 200, inclusive.

In accordance with another aspect of the invention, there are provided cosmetics or toiletries and ointments which contain ethylene oxide adducts of the above general formula (I).

In accordance with a further aspect of the invention, there is provided a method of producing ethylene oxide adducts of the general formula (I) which comprises reacting 2,6,10,15,19,23-hexamethyltetracosane-10,15-diol with ethylene oxide in the presence of an alkali metal or an alcoholate thereof.

DETAILED DESCRIPTION OF THE INVENTION

In the above general formula, the mean value of the sum of m and n, which indicates the average amount of ethylene oxide added, falls within the range of 10 to 200, inclusive. As will be mentioned later herein, the mean value of the sum of m and n preferably falls within the range of 50 to 150, inclusive, from the viewpoint of feel and touch characteristics of the ethylene oxide adducts of general formula (I).

The alkali metal or alcoholate thereof to be caused to be present in the reaction system in effecting the reaction between 2,6,10,15,19,23-hexamethyltetracosane-10,15-diol and ethylene oxide in accordance with the invention is, for example, sodium, potassium, sodium methylate, sodium ethylate, potassium isopropylate, potassium tert-butylate or potassium tert-amylate. Such alkali metal or alcoholate thereof is used in an amount of about 0.1–2.5% by weight, preferably about 0.2–1.5% by weight, based on 2,6,10,15,19,23-hexamethyltetracosane-10,15-diol. This reaction is carried out generally at a temperature within the range of about 100°–180° C. and at a pressure not exceeding about 5 kg/cm² (gage). In carrying out the method of the invention, it is preferable to charge a reactor with 2,6,10,15,19,23-hexamethyltetracosane-10,15-diol and an appropriate amount of an alkali metal or an alcoholate thereof, then introduce about 10–200 moles of ethylene oxide per mole of 2,6,10,15,19,23-hexamethyltetracosane-10,15-diol into the reactor under pressure, and allow the reaction to proceed under the above-mentioned reaction conditions.

After completion of the reaction, the remaining ethylene oxide is purged from the reaction mixture, whereby the ethylene oxide adducts of general formula (I) are obtained. In that case, the ethylene oxide adducts of general formula (I) so obtained may contain unreacted 2,6,10,15,19,23-hexamethyltetracosane-10,15-diol depending on the reaction conditions employed. When the content of the unreacted 2,6,10,15,19,23-hexamethyltetracosane-10,15-diol in the ethylene oxide adducts of general formula (I) is high, turbidity may probably be encountered upon dissolution of said ethylene oxide adducts in water. For their use as base components in water-alcohol system-based liquid cosmetics to be mentioned later herein, therefore, the ethylene oxide adducts of general formula (I) are preferably rid of the unreacted 2,6,10,15,19,23-hexamethyltetracosane-10,15-diol as far as possible. Preferred to this end is the method of removing the unreacted 2,6,10,15,19,23-hexamethyltetracosane-10,15-diol which comprises extracting the same with a hydrocarbon solvent such as n-hexane, n-heptane or isooctane. The thus-obtained ethylene oxide adducts of general formula (I) contain alkali metal alcoholate in trace amounts but can be used as they are as base components in cosmetics or ointments. They may be neutralized with an acid such as acetic acid or citric acid, as occasion demands.

The ethylene oxide adducts of general formula (I) have excellent feel and touch characteristics similar to those possessed by squalane which is so far in wide use as a base component in cosmetics. Thus, they exhibit those light feel and touch characteristics which are currently popular, such as (1) nonstickiness, (2) good spreadability, (3) plainness without oiliness or greasiness, (4) ability to give a feeling of absorption and permeation, (5) good compatibility, (6) lack in ability to cause hot sensation, (7) lack in glaringness and (8) satisfactory smoothness, when they are applied to the skin. They are not irritant to the skin, have good stability in air and, unlike squalane, are soluble in water. These favorable properties make the ethylene oxide adducts of general formula (I) useful as base components in various cosmetics or ointments. Since, in particular, they are soluble in water, the ethylene oxide adducts of general formula (I) are preferably used as base components in water-alcohol system-based liquid cosmetics, such as lotion, hair tonic and toilet water. The ethylene oxide adducts of general formula (I) can also be formulated readily in hair care preparations such as shampoos and rinses and can condition the hair and at the same time can be effective in rendering the hair oily.

Furthermore, the ethylene oxide adducts of general formula (I) are surface-active and it is possible, by taking advantage of this property, to use them as emulsifying agents in creams, milk lotions and the like and also as solubilizing agents for perfumes, oil-soluble base components and so forth in the above-mentioned liquid cosmetics.

The cosmetics and ointments provided by the present invention are characterized in that they contain (or are formulated so as to contain) the ethylene oxide adducts of general formula (I). In producing cosmetics or ointments containing the ethylene oxide adducts, said adducts may be added, in an effective amount, to the base component system containing water and/or an oleaginous substance or substances. Generally, it is appropriate to use the ethylene oxide adducts in an amount such that they amount to about 0.01–70% by weight, preferably about 1–50% by weight, based on the whole composition (cosmetic or ointment). The above-mentioned oleaginous substance may be any of those oleaginous ones known to be usable in cosmetic or ointment formulation, for example, liquid paraffin, squalane, natural fats and oils, higher fatty acids, higher aliphatic alcohols, and esters thereof. The cosmetic or ointment compositions according to the invention may contain, in addition to the above, any of materials generally incorporated or incorporable into cosmetics or ointments. Examples of such materials are moisturizers, thickeners, preservatives, emulsifiers, pharmacologically active ingredients, perfumes, and emulsion stabilizers.

The cosmetics according to the invention include, among others, liquid ones such as toilet water, hair tonics, Eau de Cologne, and perfumes; powder-form ones such as face powders, and talcum powders; emulsion-form ones such as creams, milk lotions, and hair creams; compound ones such as toilet water containing powdery components, and liquid face powders; jelly-like ones such as creams, shampoos and packs; paste-like ones such as foundations and toothpastes; stick-form ones such as hair sticks, lipsticks and stick-form makeup preparations; cake-form ones such as compact face powders, pressed preparations, and cheek rouges; pencil-form ones such as eyebrow pencils, eye liners and lip pencils; aerosol type ones such as hair sprays, shaving creams, Eau de Colonge and perfumes; and soap products such as solid soap and creamy soap.

EXAMPLES

The following examples are directed to the production of several ethylene oxide adduct species according to the invention and to several cosmetic or ointment formulations according to the invention. It is to be noted, however, that these examples are by no means limitative of the scope of the invention.

PRODUCTION EXAMPLE 1

A 2-liter autoclave was charged with 150 g of 2,6,10,15,19,23-hexamethyltetracosane-10,15-diol (purity: 91.5%) and 0.8 g of sodium methylate. Then, 1,375 g of ethylene oxide was introduced into the autoclave at a temperature of 140°–160° C. and at a pressure of 1.5–2.5 kg/cm$^2$ (gage) over 5 hours. The reaction mixture was aged at the same temperature for 30 minutes, then cooled to 80° C. and depressurized to atmospheric pressure, and the remaining ethylene oxide was purged off to give 1,478 g of a light-yellow, wax-like solid (the average amount of ethylene oxide added being 100 moles/mole) having the following physical characteristics:

mp: 52°–54° C.

IR spectrum (cm$^{-1}$): 3700–3200, 3050–2650, 1460 1270, 1100, 830.

$^1$H-NMR spectrum (90 MHz) $\delta_{HMS}^{CDCl_3}$:
0.78, 0.86 (each s, 18H); 1.10 (s, 6H);
1.0–1.6 (m, 36H); 3.66 (s, 400H).

PRODUCTION EXAMPLE 2

A 2-liter autoclave was charged with 150 g of 2,6,10,15,19,23-hexamethyltetracosane-10,15-diol (purity: 91.5%) and 0.6 g of sodium methylate. Then, 825 g of ethylene oxide was introduced into the autoclave at a temperature of 140°–160° C. and at a pressure of 1.5–2.5 kg/cm$^2$ (gage) over 4 hours. The reaction mixture was aged at the same temperature for 30 minutes, then cooled to 80° C. and depressurized to atmospheric pressure, and the residual ethylene oxide was purged off to give 945 g of a light-yellow, wax-like solid (the average amount of ethylene oxide added being 60 moles/mole) having the following physical characteristics:

mp: 60°–62° C.

IR spectrum (cm$^{-1}$): 3700–3200, 3050–2650, 1460, 1270, 1100, 830.

$^1$H-NMR spectrum (90 MHz) $\delta_{HMS}^{CDCl_3}$:
0.77, 0.84 (each s, 18H); 1.08 (s, 6H);
1.0–1.6 (m, 36H); 3.62 (s, 240H).

PRODUCTION EXAMPLE 3

A 2-liter autoclave was charged with 150 g of 2,6,10,15,19,23-hexamethyltetracosane-10,15-diol (purity: 91.5%) and 1.2 g of sodium methylate. Then, 1,100 g of ethylene oxide was introduced into the autoclave at a temperature of 110°–150° C. and at a pressure of 1.0–2.0 kg/cm$^2$ (gage) over 3 hours. The reaction mixture was aged at the same temperature for 30 minutes, then cooled to 80° C. and depressurized to atmospheric pressure, and the residual ethylene oxide was purged off to give 1,213 g of a light-yellow, wax-like solid (the average amount of ethylene oxide added being 80 moles/mole) having the following physical characteristics:

mp: 55°–58° C.

IR spectrum (cm$^{-1}$): 3700–3200, 3050–2650, 1460, 1270, 1100, 830.

$^1$H-NMR spectrum (90 MHz) $\delta_{HMS}^{CDCl_3}$:
0.80, 0.87 (each s, 18H); 1.12 (s, 6H);
1.0–1.6 (m, 36H); 3.65 (s, 320H).

PRODUCTION EXAMPLE 4

A 1-liter autoclave was charged with 150 g of 2,6,10,15,19,23-hexamethyltetracosane-10,15-diol (purity: 91.5%) and 0.8 g of sodium methylate. Then, 380 g of ethylene oxide was introduced into the autoclave at a temperature of 140°–160° C. and at a pressure of 1.5–2.5 kg/cm$^2$ (gage) over 2 hours. The reaction mixture was aged at the same temperature for 30 minutes, then cooled to 80° C., and depressurized to atmospheric pressure, and the remaining ethylene oxide was purged off. The wax-like product thus obtained was placed in a 2-liter three-necked flask equipped with a reflux condenser, together with 750 g of n-hexane, and extracted with the n-hexane under reflux for 1 hour. The mixture was cooled to room temperature, the n-hexane layer was separated by decantation and the residue was dried under reduced pressure to give 506 g of a white solid (the average amount of ethylene oxide added being 75 moles/mole) having the physical characteristics given below. The n-hexane layer contained 88 g of unreacted 2,6,10,15,19,23-hexamethyltetracosane-10,15-diol.

IR spectrum (cm$^{-1}$): 3700–3200, 3050–2650, 1460, 1270, 1100, 830.

$^1$H-NMR spectrum (90 MHz) $\delta_{HMS}^{CDCl_3}$:
0.78, 0.86 (each s, 18H); 1.10 (s, 6H);
1.0–1.6 (m, 36H); 3.66 (s, 300H).

PRODUCTION EXAMPLE 5

A 2-liter autoclave was charged with 120 g of 2,6,10,15,19,23-hexamethyltetracosane-10,15-diol (purity: 91.5%) and 0.8 g of sodium methylate. Then, 1,350 g of ethylene oxide was introduced into the autoclave at a temperature of 130°–140° C. and at a pressure of 1.5–2.5 kg/cm$^2$ (gage) over 5 hours. The reaction mixture was aged at the same temperature for 30 minutes, then cooled to 80° C. and depressurized to atmospheric pressure, and the remaining ethylene oxide was purged off. The wax-like product thus obtained was placed in a 3-liter three-necked flask equipped with a reflux condenser, together with 750 g of n-heptane and 1.5 g of citric acid, and extraction with the n-heptane and neutralization were effected under reflux for 1 hour. The mixture was then cooled to room temperature, the n-heptane layer was separated by decantation, and the residue was dried under reduced pressure to give 1,446 g of a white solid (the average amount of ethylene oxide added being 145 moles/mole) having the physical characteristics given below. The n-heptane layer contained 14 g of unreacted 2,6,10,15,19,23-hexamethyltetracosane-10,15-diol.

IR spectrum (cm$^{-1}$): 3700–3200, 3050–2650, 1460, 1270, 1100, 830.

$^1$H-NMR spectrum (90 MHz) $\delta_{HMS}^{CDCl_3}$:
0.77, 0.85 (each s, 18H); 1.10 (s, 6H);
1.0–1.6 (m, 36H); 3.65 (s, 580H).

PRODUCTION EXAMPLE 6

A 1-liter autoclave was charged with 200 g of 2,6,10,15,19,23-hexamethyltetracosane-10,15-diol (purity: 91.5%) and 1.0 g of sodium methylate. Then, 330 g of ethylene oxide was introduced into the autoclave at a temperature of 140°–150° C. and at a pressure of 1.5–2.5 kg/cm$^2$ (gage) over 1 hour. The reacton mixture was aged at the same temperature for 30 minutes and, then, cooled to 80° C. and depressurized to atmospheric pressure, and the remaining ethylene oxide was purged off. The wax-like product thus obtained was placed in a 2-liter three-necked flask equipped with a reflux condenser, together with 500 g of n-hexane and 1.6 g of citric acid, and extraction with the n-hexane and neutralization were effected under reflux for 1 hour. The mixture was cooled to room temperature, the n-hexane layer was separated by decantation, and the residue was dried under reduced pressure to give 390 g of a white solid (the average amount of ethylene oxide added being 54 moles/mole) having the physical characteristics given below. The n-hexane layer contained 118 g unreacted 2,6,10,15,19,23-hexamethyltetracosane-10,15-diol.

IR spectrum (cm$^{-1}$): 3700–3200, 3050–2650, 1460, 1270, 1100, 830.

$^1$H-NMR spectrum (90 MHz) $\delta_{HMS}^{CDCl_3}$:
0.77, 0.85 (each s, 18H); 1.10 (s, 6H);
1.0–1.6 (m, 36H); 3.6 (s, 216H).

FORMULATION EXAMPLE 1

| Toilet water (for cleansing) | |
| --- | --- |
| Materials | Weight % |
| Ethyl alcohol | 10.0 |
| Perfume | 0.1 |
| Ethylene oxide adduct of Production Example 1 | 1.0 |
| 1,3-Butylene glycol | 3.0 |
| Preservative (parahydroxybenzoic acid ester) | q.s. |
| Color (Yellow No. 4, Blue No. 1) | q.s. |
| Purified water | 85.9 |

The above perfume and preservative were dissolved in the alcohol. Separately, the water-soluble materials were dissolved in purified water. Both the solutions were mixed and filtered. The above materials showed good compatibility with each other and the product obtained was homogeneous. When applied to the skin, this product proved to be significantly better in the feel and touch characteristics (1) to (8) mentioned hereinabove as compared with a toilet water having the same composition as given above except for the absence of the ethylene oxide adduct. It was not irritant to the skin.

Toilet waters (for cleansing) were prepared by using the same amount of each of the ethylene oxide adducts obtained in Production Examples 2 to 6 in place of the above ethylene oxide adduct of Production Example 1. They had the same excellent feel and touch characteristics and were not irritant to the skin.

FORMULATION EXAMPLE 2

| Toilet water (for general use) | |
|---|---|
| Materials | Weight % |
| Ethyl alcohol | 8.0 |
| Perfume | 0.1 |
| Ethylene oxide adduct of Production Example 1 | 0.5 |
| Glycerin | 2.0 |
| 70% Aqueous solution of sorbitol | 2.0 |
| Sodium pyrrolidonecarboxylate | 3.0 |
| Sodium citrate | 0.1 |
| Citric acid | 0.2 |
| Preservative (parahydroxybenzoic acid ester) | q.s. |
| Color (Yellow No. 4, Blue No. 1) | q.s. |
| Purified water | 84.1 |

A toilet water was prepared in the same manner as in Formulation Example 1. The above materials exhibited good compatibility with each other and the product obtained was homogeneous. When applied to the skin, this product proved to be significantly better in the feel and touch characteristics (1) to (8) mentioned above as compared with a toilet water having the same composition as given above except for the absence of the ethylene oxide adduct.

Toilet waters (for general use) were prepared by using the same amount of each of the ethylene oxide adducts obtained in Production Examples 2 to 6 in place of the above ethylene oxide adduct of Production Example 1. They had the same excellent feel and touch characteristics and were not irritant to the skin.

FORMULATION EXAMPLE 3

| Hair tonic | |
|---|---|
| Materials | Weight % |
| Ethyl alcohol | 60.0 |
| l-Menthol | 0.2 |
| Glycyrrhetin | 0.1 |
| Pantothenyl alcohol | 0.2 |
| dl-α-Tocopheryl acetate | 0.05 |
| Ethylene oxide adduct of Production Example 1 | 1.0 |
| Perfume | 0.2 |
| 1,3-Butylene glycol | 2.0 |
| Preservative (parahydroxybenzoic acid ester) | q.s. |
| Color (Yellow No. 4, Blue No. 1) | q.s. |
| Purified water | 36.25 |

The above materials were mixed together to make a solution, followed by filtration. The above materials exhibited good compatibility with each other and the product obtained was homogeneous. When applied to the hair, the product well made the hair satisfactorily oily.

Hair tonics were prepared by using the same amount of each of the ethylene oxide adducts obtained in Production Examples 2 to 6 in place of the above ethylene oxide adduct of Production Example 1. When applied to the hair, they were also satisfactorily effective in rendering the hair oily.

FORMULATION EXAMPLE 4

| Hair liquid | |
|---|---|
| Materials | Weight % |
| Polypropylene glycol butyl ether | 20.0 |
| Ethylene oxide adduct of Production Example 1 | 1.0 |
| Polypeptide ethyl ester | 0.5 |
| Ethyl alcohol | 60.0 |
| Perfume | 0.5 |
| Color (Yellow No. 4, Blue No. 1) | q.s. |
| Preservative (parahydroxybenzoic acid ester) | q.s. |
| Purified water | 18.0 |

The above materials were mixed together to make a solution, followed by filtration. The above materials showed good compatibility with each other and the product obtained was homogeneous. When applied to the hair, this product conditioned the hair satisfactorily and also made the hair satisfactorily oily.

Hair liquids were prepared by using the same amount of each of the ethylene oxide adducts obtained in Production Examples 2 to 6 in place of the above ethylene oxide adduct of Production Example 1. When applied to the hair, they also conditioned the hair satisfactorily and made the hair satisfactorily oily.

FORMULATION EXAMPLE 5

| Cream shampoo | |
|---|---|
| Materials | Weight % |
| Sodium polyoxyethylene lauryl sulfate | 25.0 |
| Triethanolamine lauryl sulfate | 15.0 |
| Coconut oil fatty acid diethanolamide | 4.0 |
| Ethylene oxide adduct of Production Example 1 | 1.0 |
| Ethylene glycol monostearate | 1.5 |
| 1,3-Butylene glycol | 1.0 |
| Disodium edetate | 0.1 |
| Purified water | 52.2 |
| Perfume | 0.2 |
| Preservative (parahydroxybenzoic acid ester) | q.s. |
| Color (Yellow No. 4, Blue No. 1) | q.s. |

The above materials were mixed with heating (75° C.) until dissolution and, then, the mixture was cooled to room temperature. The above materials were sufficiently compatible with each other and the product obtained was homogeneous. When applied to the hair, this product made the hair satisfactorily oily.

Cream shampoos were prepared by using the same amount of each of the ethylene oxide adducts obtained in Production Examples 2 to 6 in place of the above ethylene oxide adduct of Production Example 1. When applied to the hair, they also made the hair satisfactorily oily.

FORMULATION EXAMPLE 6

| Cream rinse | |
|---|---|
| Materials | Weight % |
| Stearyltrimethylammonium chloride | 4.0 |
| Cetyl alcohol | 3.0 |

-continued

Cream rinse

| Materials | Weight % |
| --- | --- |
| Glycerol monostearate | 5.0 |
| Ethylene oxide adduct of Production Example 1 | 2.0 |
| Octyldodecanol | 2.0 |
| 1,3-Butylene glycol | 1.0 |
| Purified water | 82.8 |
| Perfume | 0.2 |
| Preservative (parahydroxybenzoic acid ester) | q.s. |
| Color (Yellow No. 4, Blue No. 1) | q.s. |

Of the above materials, the oleaginous or oil-soluble ones, on one hand, and the aqueous or water-soluble ones, on the other hand, were respectively mixed and heated (75° C.) to make solutions, the solutions were mixed for emulsification, and the emulsion was cooled to room temperature. The above materials were well compatible with each other and the product obtained was homogeneous. When applied to the hair, this product produced a good effect in rendering the hair oily.

Cream rinses were prepared by using the same amount of each of the ethylene oxide adducts obtained in Production Examples 2 to 6 in place of the above ethylene oxide adduct of Production Example 1. When used in hair rinsing, they also produced a good effect in making the hair oily.

FORMULATION EXAMPLE 7

Cream (weakly oleaginous nourishing cream)

| | Materials | Weight % |
| --- | --- | --- |
| (1) | Stearic acid | 9.0 |
| | Cetyl alcohol | 3.5 |
| | Spermaceti | 2.5 |
| | Lanolin | 2.0 |
| | 2-Octyldodecyl myristate | 10.0 |
| | Ethylene oxide adduct of Production Example 1 | 4.0 |
| (2) | Preservative (parahydroxybenzoic acid ester) | q.s. |
| | Propylene glycol | 3.0 |
| | Triethanolamine | 0.5 |
| | Purified water | 65.5 |
| (3) | Perfume | q.s. |

The materials given under (2) were mixed with heating (75°-80° C.) to make a solution. Thereto was added a solution prepared by mixing the materials given under (1) with heating (75°-80° C.) The perfume (3) was added to the resulting emulsion and the whole mixture was cooled to room temperature. The above materials were well compatible with each other and the product obtained was homogeneous. When applied to the skin, this product proved to be significantly better in the above-mentioned feel and touch characteristics (1) to (8) as compared with a cream having the same composition as given above except for the absence of the ethylene oxide adduct.

Creams were prepared by using the same amount of each of the ethylene oxide adducts obtained in Production Examples 2 to 6 in place of the above ethylene oxide adduct of Production Example 1. They also had the same excellent feel and touch characteristics as the above-mentioned cream had.

FORMULATION EXAMPLE 8

Ointment base

| | Materials | Weight % |
| --- | --- | --- |
| (1) | Sorbitol sesquioleate (Arlacel C) | 2.5 |
| | Cerecin | 7.5 |
| | Vaselin | 10.0 |
| | Ethylene oxide adduct of Production Example 1 | 10.0 |
| | Lanolin | 5.0 |
| (2) | Purified water | 25.0 |

The materials given above under (1) were mixed with heating (75°-80° C.) to make a solution. Thereto was added with stirring the purified water (2) heated to 80° C. The whole mixture was then cooled to room temperature. The above materials were well compatible with each other and the product obtained was homogeneous. When applied to the skin, this product was significantly good in the above-mentioned feel and touch characteristics.

Ointment bases were prepared by using the same amount of each of the ethylene oxide adducts obtained in Production Examples 2 to 6 in place of the above ethylene oxide adduct of Production Example 1. They also had the same excellent feel and touch characteristics as the above-mentioned ointment base had.

What is claimed is:

1. An ethylene oxide adduct of the formula

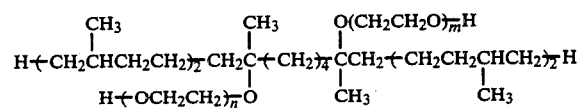

wherein the means value of the sum of m and n falls within the range of 10 to 200, inclusive.

2. The ethylene oxide adduct of claim 1, wherein the mean value of the sum of m and n appearing in the general formula falls within the range of 50 to 150, inclusive.

3. A cosmetic or ointment which contains a cosmetically effective amount of an ethylene oxide adduct of the formula

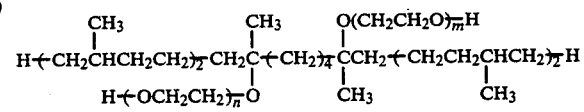

wherein the mean value of the sum of m and n falls within the range of 10 to 200, inclusive and water, at least one oleaginous substance or mixtures thereof 4. The cosmetic or ointment of claim 3, wherein the mean value of the sum of m and n appearing in the general formula falls within the range of 50 to 150, inclusive.

* * * * *